United States Patent [19]
Müller et al.

[11] Patent Number: 4,659,916
[45] Date of Patent: Apr. 21, 1987

[54] ARRANGEMENT FOR CORRECTING THE POSITION OF A LASER BEAM GUIDED BY MEANS OF AN ARTICULATED OPTICAL SYSTEM

[75] Inventors: Gerhard Müller, Aalen; Gerhard Hohberg, Oberkochen; Peter Greve, Essingen, all of Fed. Rep. of Germany

[73] Assignee: Carl-Zeiss-Stiftung, Heidenheim, Fed. Rep. of Germany

[21] Appl. No.: 701,168

[22] Filed: Feb. 13, 1985

[30] Foreign Application Priority Data

Feb. 24, 1984 [DE] Fed. Rep. of Germany ....... 3406676

[51] Int. Cl.$^4$ .................. G05D 3/12; G02B 17/06; B23K 26/04
[52] U.S. Cl. ................ 250/201; 219/121 LV
[58] Field of Search ................ 219/121 LU, 121 LV, 219/121 LW, 121 LX; 250/201, 202, 205; 369/44, 45, 46

[56] References Cited

U.S. PATENT DOCUMENTS

| 3,902,036 | 8/1975 | Zaleckas | 219/121 LX |
|---|---|---|---|
| 4,114,180 | 9/1978 | Kayanuma | 250/205 |
| 4,271,334 | 6/1981 | Yardy | 369/44 |
| 4,279,472 | 7/1981 | Street | 250/201 |
| 4,349,732 | 9/1982 | Whitby et al. | 250/201 |
| 4,429,211 | 1/1984 | Carstens et al. | 219/121 LV |
| 4,482,987 | 11/1984 | Okada et al. | 369/44 |
| 4,535,431 | 8/1985 | Bricot et al. | 250/202 |

FOREIGN PATENT DOCUMENTS

| 0102695 | 8/1979 | Japan | 219/121 LX |
|---|---|---|---|
| 0224088 | 12/1983 | Japan | 219/121 LU |

*Primary Examiner*—Edward P. Westin
*Assistant Examiner*—Charles Weiland
*Attorney, Agent, or Firm*—Walter Ottesen

[57] ABSTRACT

The invention is directed to an arrangement for correcting the position of a laser beam guided by means of an articulated optical system. This system includes a position-sensitive detector at its output end for generating a signal which is passed to an adjustable mirror arranged on the input end. The adjustable mirror compensates for an excursion of the laser beam occurring as a result of faults in the guide means and bearings of the articulated arm. Prior to entering the articulated optical system, the laser beam or parallelly guided pilot beam is modulated with respect to the beam direction with a small amplitude by another adjustable mirror. The detector signal component corresponding to the modulation frequency is passed to an electronic circuit which determines the directional relationships between the excursion of the laser beam at the output of the articulated arm and the follow-up movement of the adjustable mirror for deflecting the beam. This determination is achieved independently of the amount of rotation of the rotational bearings.

8 Claims, 1 Drawing Figure

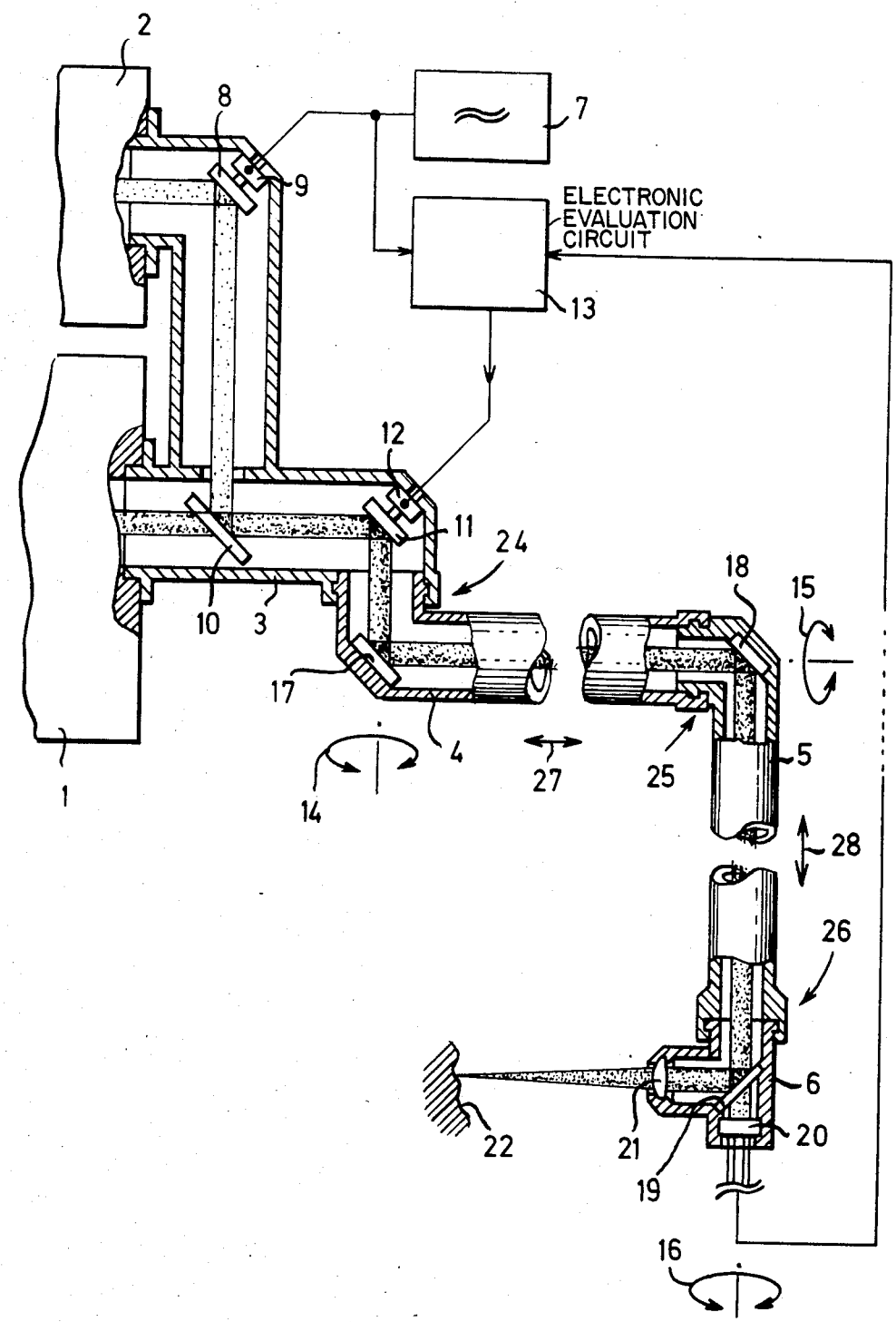

ARRANGEMENT FOR CORRECTING THE POSITION OF A LASER BEAM GUIDED BY MEANS OF AN ARTICULATED OPTICAL SYSTEM

BACKGROUND OF THE INVENTION

For guiding laser beams, it is customary to use either light conductors in the form of flexible glass fibers or transmission systems containing optical deflectors such as mirrors. Particularly in medical applications such as laser surgery, for example, articulated transmission systems of the last-mentioned type are frequently used because so far there are no fiber cables which are sufficiently resistant to rupture while at the same time providing for a sufficiently low-loss transmission in the wavelength range of the carbon-dioxide lasers predominantly used in these applications.

The articulated arms used for guiding the laser beam include a series of deflection mirrors secured to rotatable joints such that each mirror is rotatable about the axis of the incident laser beam together with the follow-on part of the pivot arm. In addition, telescope guides are often inserted between the joints thereby enabling the length of the arm to be changed. Articulated arms having as many as seven rotatable joints are known.

Apart from being dependent on a sufficiently precise adjustment of the mirrors, the proper function of such an articulated arm depends on the quality of the pivot bearings and telescopic guides as well as on the rigidity of their connections. The problems associated therewith become greater as the dimensions of the work area covered by the articulated arm increase. Adding more rigidity to the arm requires stronger material and, accordingly, larger masses to be moved. This puts an increased load on the pivot bearings and impairs handling, particularly in dynamic operation.

If, however, guidance errors occur, the beam will wander from its predetermined beam path. First of all, this will cause the laser focus to shift which is not particularly disturbing within certain limits, especially if the focus position is visually evaluated by means of a reflected pilot beam. Where long articulated arms are used, the situation can occur that the laser beam within the articulated optical system wanders out of the free openings of the deflection mirrors or the focusing optics and impinges on their mountings. In this event, high-performance lasers will destroy the optical system.

In laser systems for reading out the contents of information storage plates, it is known to provide control arrangements which make the focus of the laser beam follow a predetermined track radially. These control arrangements, however, evaluate the deviation of the focus from the visibly marked data track. In addition, there exists a fixed spatial relationship between the direction of movement of the positioning member and that of the laser focus. However, if the laser beam is guided via several articulated joints, the angle of rotation of each individual joint has to be taken into consideration when determining the relationship between the position coordinates of the focus and the positioning coordinates of the member performing the follow-up function. This is not easily possible since the complexity of the arrangement would increase considerably if each articulated joint were provided with an angle sensor of its own, particularly in articulated arms including several pivot axes.

SUMMARY OF THE INVENTION

It is the object of the invention to provide, with a minimum possible amount of complexity, an articulated optical system for a power laser which is of light-weight construction and permits a sufficiently stable guidance of the laser beam without making too stringent demands on the quality of the bearings used.

This object is achieved by the invention in that the laser beam, prior to entering the articulated optical system, is directed via an optical member modulating the direction of the beam with a small amplitude, in that part of the laser beam is directed to a position-sensitive detector arranged on the output side of the articulated optical system, and in that a circuit is provided which receives the detector signal for generating a control signal which is applied to a controllable beam deflector arranged on the input side of the articulated optical system.

Accordingly, the arrangement of the invention compensates for deviations of the laser beam from the axis of the articulated optical system. The deviations are determined at the output of the articulated optical system and the compensation is performed by means of a beam deflector arranged at the input of the system. As a result, it is possible to use bearings for the arm which are manufactured to reduced standards of quality and less emphasis has to be placed on rigidity of the system. Also, costs are saved by reducing the requirements for guiding accuracy. The savings in costs exceed by far the additional expenditure caused by the elements for controlling the beam position.

The modulation of the beam direction at the input of the articulated optical system generates alternating signals on the receiver at the output which have an amplitude and phase position that make possible a definitive directional coordination. Because of this modulation, the beam position can always be correctly adjusted, in spite of the rotational movements occurring in the articulated arm and irrespective of the number of articulated joints utilized.

The element modulating the beam direction, which is preferably a piezoelectrically deflectable mirror, may at the same time be used as the positioning member for controlling the beam position. This is accomplished by superposing the control signal on the alternating signal of the modulation frequency.

If, however, an auxiliary or pilot laser, which is anyway used for visual recognition of the focus, is introduced via a mirror coaxially with the beam of the actual work laser, then it is suitable to arrange the modulating optical element in the beam path of the pilot laser prior to coupling the pilot laser beam into the beam path of the work laser and to provide a separate positioning member in the common beam path of the two laser beams. Known photoelectric quadrant receivers may be advantageously used as position-sensitive detectors.

Further advantageous embodiments of the invention will become apparent from the subsequent description in conjunction with the drawing.

BRIEF DESCRIPTION OF THE DRAWING

The invention will now be described with reference to the drawing which is a schematic of an articulated optical system equipped with an embodiment of the arrangement according to the invention for correcting the position of the laser beam guided in the system.

DESCRIPTION OF THE PREFERRED EMBODIMENTS OF THE INVENTION

In the drawing, reference numeral 1 identifies the housing of a carbon-dioxide laser whose beam is directed via an articulated arm to a focusing lens 21. Focusing lens 21 is manually movable in several degrees of freedom and focuses the beam onto the surface of an object 22 not specified in more detail. The articulated optical system includes: a positionally fixed tube 3 flange connected to the housing 1; a second telescopically expandable tube 4 connected with tube 3 by means of a first rotational bearing 24 for permitting rotational movement; a third telescopically expandable tube 5 connected with tube 4 by means of a second rotational bearing 25; and, a cutting head 6 which accommodates the focusing lens 21 and is secured to tube 5 by means of a third rotational bearing 26. While arrows 14, 15 and 16 indicate the direction of rotation of bearings 24, 25 and 26, arrows 27 and 28 illustrate the directions in which the respective telescopically expandable parts 4 and 5 move.

Parts 4, 5 and 6 of the articulated arm are angled behind the respective ones of the rotational bearings 24, 25 and 26 about which they are rotatable with their follow-on parts. The parts 4, 5 and 6 accommodate deflection mirrors 17, 18 and 19, respectively, and guide the laser beam in the articulated arm. Further, positionally fixed part 3 of the articulated arm contains a wavelength-selective beam splitter 10 by means of which the beam of a pilot laser 2 is coupled into the articulated arm coaxially with the beam of the work laser 1. Pilot laser 2 indicates to the operator guiding the articulated arm the focus position of the invisible beam of the work laser 1 on the surface of the object 22. Mirror 19 via which work laser 1 is reflected into focusing lens 21 is likewise configured as a beam splitter and permits the unreflected passage of part of the beam of pilot laser 2 for impingement on a photoelectric quadrant detector 20 arranged behind the mirror.

The photosensitive surface of detector 20 is subdivided into four sectors of equal size. These sectors issue dc signals the amplitudes of which will not differ so long as the component beam of laser 2 passed unreflected by mirror 19 impinges centrically on detector 20. As soon as the component beam deviates from the centric position which, for example, may be due to slight deformations of the telescope guides on movement of the articulated arm or due to runout of rotational bearings 24 to 26, the amplitude relationships of the dc signals of the four quadrants will change. This change is a measure of the amount of excursion of the laser beam directed through the arm relative to the axis of the articulated optical system. An electronic circuit 13 evaluates the dc signals and generates a corrective positioning signal which is applied to an adjustable mirror 11 arranged at the input of the articulating arm. The deflection of adjustable mirror 11 will compensate for the excursion of the laser beam.

Adjustable mirror 11 is secured to part 3, which is fixedly secured to the housing, with piezo elements 12 interposed therebetween. It is to be understood that the adjustment of the position of mirror 11 can also be accomplished using, for example, inductive positioning members. It is only essential that mirror 11 is adjustable in two coordinates.

Because of the absence of a rigid connection between detector 20 and adjustable mirror 11 and because the direction in which mirror 11 deflects the laser beam to compensate for the determined beam excursion is dependent on the angle of rotation of the three rotational bearings 24, 25 and 26, a second adjustable mirror 8 is provided in the beam path of pilot laser 2 in front of beam splitter 10. Adjustable mirror 8 includes a piezoelectric bending element 9 which is periodically energized by a generator 7 and thus modulates the beam of the auxiliary laser 2 with respect to the beam direction with a small amplitude.

In view of this periodic modulation of the beam direction of pilot laser 2, the sectors of detector 20, in addition to supplying the dc signal, also deliver an ac signal. From the amplitude relationship and phase position of this signal with reference to the output signal of generator 7, the rotational position of adjustable mirror 11 relative to detector 20 can be determined. This evaluation is likewise performed by electronic circuit 13. The corrective positioning signal generated for mirror 11 by circuit 13 thus causes this mirror to be adjusted by magnitude and direction such that the component beam of laser 2 passing through beam splitter 19 impinges centrically upon detector 20.

The circuit 13 for evaluation of the ac and dc signals of detector 20 may be implemented in various ways. For example, the embodiment chosen depends on whether the modulation movement of adjustable mirror 8 is linear or precessive.

Embodiments for piezoelectrically operating adjustable mirrors are described, among others, in German Pat. No. 29 50 919.

It is understood that the foregoing description is that of the preferred embodiments of the invention and that various changes and modifications may be made thereto without departing from the spirit and scope of the invention as defined in the appended claims.

What is claimed is:

1. An arrangement for correcting the position of a laser beam having a multiplicity of rays and guided by means of an articulated optical system defining an optical axis and including a plurality of arm segments pivotally connected one to the other at respective pivot joints so as to define an articulated arm having an input end and an output end, the articulated arm being subjected to deformations and the like which can cause the laser beam to deviate from said optical axis, the arrangement comprising:

optical modulating means for modulating the laser beam with respect to its direction before said laser beam enters the input end of the articulated arm;

a plurality of deflectors disposed at corresponding ones of said joints for guiding said laser beam along said articulated arm and which can be subjected to an unwanted tilt against said optical axis as a consequence of said deformations;

beam splitter means for splitting off a portion of the rays of the laser beam to form a component beam;

position-sensitive detector means arranged at the output end of said articulated arm for receiving said component beam thereon and for generating electrical signals in response to a deviation of said component beam from said optical axis and providing a measure of the cumulative effect of the degree of rotation between the input end and the output end of said articulated arm;

a control unit for receiving said electrical signals of said detector means and for generating a control signal for correcting said deviation and compensating for said unwanted tilt in a direction determined according to the measured degree of rotation; and, adjustable beam deflecting means arranged at the imput end of said articulated arm for adjusting the position of said laser beam in response to said control signal.

2. The arrangement of claim 1, said optical modulating means being adapted to also deflect the laser beam.

3. The arrangement of claim 1, said position-sensitive detector means being a quadrant receiver.

4. The arrangement of claim 1, said adjustable beam deflecting means and said optical modulating means each being configured as adjustable piezoelectric deflecting mirrors.

5. An arrangement for correcting the position of a work laser beam guided by means of an articulated optical system defining an optical axis and including a plurality of arm segments pivotally connected one to the other at respective pivot joints so as to define an articulated arm having an input end and an output end, the articulated arm being subjected to deformations and the like which can cause the work laser beam to deviate from said optical axis, the arrangement comprising:

pilot laser beam generating means for generating a pilot laser beam having a multiplicity of rays;

first deflecting means for coupling said pilot laser beam into said articulated arm so as to follow said optical axis;

optical modulating means for modulating said pilot laser beam with respect to its direction before said laser beam enters the input end of the articulated arm;

a plurality of deflectors disposed at corresponding ones of said joints for guiding said laser beams along said articulated arm and which can be subjected to an unwanted tilt against said optical axis as a consequence of said deformations;

beam splitter means for splitting off a portion of the rays of said pilot laser beam to form a component beam;

position-sensitive detector means arranged at the output end of said articulated arm for receiving said component beam thereon and for generating electrical signals in response to a deviation of said component beam from said optical axis and providing a measure of the cumulative effect of the degree of rotation between the input end and the output end of said articulated arm;

a control unit for receiving said electrical signals of said detector means and for generating a control signal for correcting said deviation and compensating for said unwanted tilt in a direction determined according to the measured degree of rotation; and, adjustable beam deflecting means arranged at the input end of said articulated arm for adjusting the position of said laser beams in response to said control signal.

6. The arrangement of claim 5, said optical modulating means being an amplitude modulating device and being disposed in the path of said pilot laser beam ahead of said beam splitter means.

7. The arrangement of claim 6, said position-sensitive detector means being a quadrant receiver.

8. The arrangement of claim 6, said adjustable beam deflecting means and said optical modulating means each being configured as adjustable piezoelectric deflecting mirrors.

* * * * *